US012016802B2

(12) United States Patent
Kirschman

(10) Patent No.: US 12,016,802 B2
(45) Date of Patent: Jun. 25, 2024

(54) AIR TREATMENT SYSTEM FOR OPERATING OR PATIENT ROOMS

(71) Applicant: David Louis Kirschman, Dayton, OH (US)

(72) Inventor: David Louis Kirschman, Dayton, OH (US)

(73) Assignee: Aerobiotix. LLC, Miamisburg, OH (US)

( * ) Notice: Subject to any disclaimer, the term of this patent is extended or adjusted under 35 U.S.C. 154(b) by 382 days.

(21) Appl. No.: 16/910,363

(22) Filed: Jun. 24, 2020

(65) Prior Publication Data

US 2021/0113407 A1    Apr. 22, 2021

Related U.S. Application Data

(60) Provisional application No. 62/924,251, filed on Oct. 22, 2019.

(51) Int. Cl.
| | | |
|---|---|---|
| *A61G 13/10* | (2006.01) | |
| *A61B 90/00* | (2016.01) | |
| *A61G 10/02* | (2006.01) | |
| *A61L 9/00* | (2006.01) | |
| *B01D 46/00* | (2022.01) | |
| *F24F 3/16* | (2021.01) | |

(52) U.S. Cl.
CPC ............ *A61G 13/108* (2013.01); *A61B 90/00* (2016.02); *A61G 10/02* (2013.01); *A61L 9/00* (2013.01); *B01D 46/00* (2013.01); *F24F 3/16* (2013.01)

(58) Field of Classification Search
CPC ............................ B01D 46/00; A61G 13/108
See application file for complete search history.

(56) References Cited

U.S. PATENT DOCUMENTS

| | | | |
|---|---|---|---|
| 3,107,863 A | * | 10/1963 | Potapenko ........... A61G 13/108 607/83 |
| 3,726,203 A | | 4/1973 | Lindestrom |
| 3,803,995 A | | 4/1974 | Allander |
| 3,998,142 A | | 12/1976 | Foreman et al. |
| 4,009,647 A | | 3/1977 | Howorth |
| 4,055,112 A | | 10/1977 | Larkfeldt |
| 4,094,232 A | | 6/1978 | Howorth |
| 4,137,831 A | | 2/1979 | Howorth |
| 4,164,173 A | | 8/1979 | Douglas |
| 4,267,769 A | | 5/1981 | Davis et al. |
| 4,381,380 A | | 4/1983 | LeVeen et al. |
| 4,476,590 A | | 10/1984 | Scales et al. |
| 4,563,485 A | | 1/1986 | Fox, Jr. et al. |
| 4,592,920 A | | 6/1986 | Murtfeldt |
| 4,603,152 A | | 7/1986 | Laurin et al. |
| 4,612,337 A | | 9/1986 | Fox, Jr. et al. |

(Continued)

FOREIGN PATENT DOCUMENTS

| | | | | |
|---|---|---|---|---|
| WO | WO-2010100559 A1 | * | 9/2010 | ........... A61G 13/108 |
| WO | 2018104955 | | 6/2018 | |

*Primary Examiner* — Robert A Hopkins
(74) *Attorney, Agent, or Firm* — Jacox, Meckstroth & Jenkins

(57) ABSTRACT

An operating room air treatment system and method for handling airflow in zones in an operating room. The system provides a substantially vertical air flow zone that is located generally peripherally to the operating room table and a substantially central airflow zone that is located generally centrally in the operating room.

13 Claims, 7 Drawing Sheets

(56) References Cited

U.S. PATENT DOCUMENTS

| | | |
|---|---|---|
| 4,615,705 A | 10/1986 | Scales et al. |
| 4,708,870 A | 11/1987 | Pardini |
| 4,849,223 A | 7/1989 | Pratt et al. |
| 4,890,544 A | 1/1990 | Aalto et al. |
| 4,925,668 A | 5/1990 | Khan et al. |
| 4,929,262 A | 5/1990 | Balon, Jr. et al. |
| 4,933,178 A | 6/1990 | Capelli |
| 5,013,306 A | 5/1991 | Solomon et al. |
| 5,019,096 A | 5/1991 | Fox, Jr. et al. |
| 5,180,585 A | 1/1993 | Jacobson et al. |
| 5,290,330 A | 3/1994 | Tepper et al. |
| 5,302,359 A | 4/1994 | Nowatzki |
| 5,534,288 A | 7/1996 | Gruskin et al. |
| 5,830,058 A | 11/1998 | Rosjo |
| 5,858,041 A | 1/1999 | Luetkemeyer |
| 5,904,896 A | 5/1999 | High |
| 6,482,083 B1 | 11/2002 | Nilsson |
| 6,702,662 B2 | 3/2004 | Kristensson |
| 7,044,850 B2 | 5/2006 | Koch et al. |
| 8,066,802 B2 | 11/2011 | Kristensson et al. |
| 8,308,536 B2 | 11/2012 | Kristensson et al. |
| 8,465,576 B2 * | 6/2013 | Della Valle ......... A61G 13/108 55/467 |
| 10,071,177 B1 | 9/2018 | Kellogg, Jr. |
| 10,369,242 B1 | 8/2019 | Kellogg, Jr. |
| 2003/0153260 A1 | 8/2003 | Kristensson |
| 2004/0224626 A1 | 11/2004 | Koch et al. |
| 2004/0242955 A1 | 12/2004 | Koch |
| 2005/0268921 A1 | 12/2005 | Zumeris et al. |
| 2007/0254006 A1 | 11/2007 | Loose et al. |
| 2008/0099449 A1 | 5/2008 | England et al. |
| 2009/0093815 A1 | 4/2009 | Fletcher et al. |
| 2009/0288555 A1 | 11/2009 | Kristensson et al. |
| 2010/0120349 A1 | 5/2010 | Kristensson et al. |
| 2010/0291859 A1 | 11/2010 | Kristensson et al. |
| 2011/0294411 A1 | 12/2011 | Kristensson et al. |
| 2012/0085231 A1 | 4/2012 | Kristensson et al. |
| 2015/0072609 A1 | 3/2015 | Bromley |

* cited by examiner

AIR TREATMENT SYSTEM FOR OPERATING OR PATIENT ROOMS

CROSS-REFERENCE TO RELATED APPLICATION

The present application claims priority to provisional U.S. Application Ser. No. 62/924,251, filed Oct. 22, 2019, to which Applicant claims the benefit of the earlier filing date. This provisional application is incorporated herein by reference and made a part hereof.

BACKGROUND OF THE INVENTION

1. Field of the Invention

This application relates to an operating room air treatment system for controlling airflow and decontamination of an air stream having at least one of a substantially vertical air flow zone that may be located peripherally to the operating room and/or a substantially horizontal air flow zone that is located centrally in the operating room.

2. Description of the Related Art

Airborne bacteria have been shown to be a primary source of infection during surgery. Regulating the operating room environment is one of the best strategies to reduce intraoperative infections. Air flow strategies, such as laminar air flow and positive pressure, have been shown to inhibit aerobiological contamination, but these systems have limitations, as there continues to be significant air bacteriological contamination in modern operating rooms. Operating room airborne bacteria derive largely from operating room personnel. Current operating room ventilation systems typically comprise a positive pressure vertical air supply originating centrally in the ceiling of the operating room. This system creates a relative zone of higher air velocity towards the center of the room, and a relatively low velocity in the periphery of the room. Similarly, there is cleaner, higher velocity air in the central zone of the room, and slower, dirtier air in the periphery of the operating room. These low-flow peripheral "dead zones" can be reservoirs for airborne bacteria which can be carried by airflow currents, pressure, surface vector such as instrumentation, surgical gowns or gloves, to the surgical site.

What is needed, therefore, is a system and method for decontaminating airflow and controlling airflow in multiple zones using a multiple zone air handling system for an operating room or patient room.

SUMMARY OF THE INVENTION

A primary object of the invention is to provide an air treatment system for improving air quality in a medical environment, such as an operating room or a patient room.

Another object of the invention is to provide a decontamination system that comprises at least one or a plurality of decontamination air handlers that are adapted to provide decontaminated air to predetermined zones in the medical environment.

Another object of the invention is to provide an air control system that provides at least one vertical column of air to a patient in a central zone of a medical environment and substantially simultaneously decontaminating air outside the central zone.

Still another object of the invention is to provide a decontamination system that decontaminates air in a peripheral zone around the patient.

Yet another object of the invention is to provide a decontamination system that decontaminates a "dirty donut" around a central zone having an operating table or bed.

Still another object of the invention is to provide a decontamination system that decontaminated air in at least one zone and returns or delivers the decontaminated air back to the same zone, such as a peripheral zone.

Still another object of the invention is to provide a decontamination system or method that reduces or eliminates cross-contamination from a peripheral zone into a central zone.

Still another object of the invention is to provide a plurality of decontamination systems and air handlers that are adapted to cooperate in order to decontaminate air in at least one or a plurality, respectively, of zones in order to reduce or eliminate cross-contamination.

Another object of the invention is to provide a first air handler that provides decontaminated air to a central zone and at least one second air handler that decontaminates air around the central zone while substantially simultaneously not contaminating or cross-contaminating the decontaminated air in the central zone.

In one aspect, the present invention is a multiple zone air handling system for an operating room which comprises a central vertical flow system and a peripheral non-vertical flow system. Furthermore, the outflow of this system is directional and/or non-turbulent in nature in at least one zone, to prevent the initiation of undesirable horizontal air currents or cross-currents, which can serve to spread contamination across a surgical field or operating table.

In another aspect, the multiple zone air handling system provides improved controls over direction, pressure, velocity, and location of air flows in all zones of the surgical operating room.

In still another aspect, one embodiment of the invention comprises a medical air treatment system for use in a medical environment having a table or bed adapted to receive a patient, the medical air treatment system comprising at least one air handler; a control for controlling operation of the at least one air handler in order to cause a first flow of air to flow substantially vertically toward or away from the table or bed and for substantially simultaneously providing a second flow of air to a peripheral zone generally surrounding the first flow of air in a manner that the second flow of air does not flow across and into the first flow of air thereby reducing or eliminating contamination of the first flow of air by the second flow of air.

In yet another aspect, one embodiment of the invention comprises an operating room air treatment system comprising a first air treatment system associated with a central zone having a table or bed for supporting a patient during treatment or a medical procedure; a second air treatment system associated with a peripheral zone that generally surrounds the central zone; and at least one control for controlling operation of the first air treatment system and the second air treatment system; the second air treatment system having an exhaust that directs a substantially decontaminated air stream into the peripheral zone such that it does not pass into the central zone.

In another aspect, another embodiment of the invention comprises an operating room air treatment system consisting of a substantially vertical air flow zone; and a substantially horizontal air flow zone; wherein the substantially vertical air flow zone is located centrally in the room and the substantially horizontal air flow zone is located peripherally in the room.

In still another aspect, one embodiment of the invention comprises an operating room air treatment system comprising a relative high velocity air zone; and a relative low velocity air zone; the treatment system withdrawing air from the low velocity zone in a directional and/or non-turbulent manner such that the purified air does not enter the high velocity zone.

In yet another aspect, one embodiment of the invention comprises an operating room air treatment system comprising a central vertical air column; and a peripheral turbulent air zone; the treatment system withdrawing air from the peripheral turbulent zone and supplying non-turbulent purified air to the peripheral turbulent zone.

In another aspect, one embodiment of the invention comprises an operating room air treatment system comprising a central vertical air column; and a peripheral turbulent air zone; the treatment system withdrawing air from the peripheral turbulent zone and supplying the purified air in a directional and/or non-turbulent manner such that the purified air does not enter the central vertical air column.

In still another aspect, one embodiment of the invention comprises an operating room air treatment system wherein the operating room comprises a central air zone in proximity to a treatment table; and a peripheral air zone in proximity to an entry door; the treatment system withdrawing air from the peripheral zone and supplying purified air in a directional and/or non-turbulent manner such that the purified air does not enter the central air zone.

In yet another aspect, one embodiment of the invention comprises an operating room air treatment system comprising a central air zone in proximity to a treatment table; and a peripheral air zone in proximity to an entry door; the treatment system withdrawing air from the peripheral zone and supplying purified air to the operating room; the purified air being non-turbulent and/or directional and non-crossing of the treatment table.

In another aspect, one embodiment of the invention comprises an operating room air treatment system comprising a central air column in proximity to obstructing features, such as lights, equipment booms or personnel; the obstructing features substantially orthogonally deflecting the air column to a peripheral air zone; the treatment system withdrawing air from the deflected air and supplying purified, non-turbulent air to the operating room.

In still another aspect, one embodiment of the invention comprises an operating room air treatment system wherein the operating room comprises an upper air zone; and a lower air zone; the lower air zone comprising air of increased contamination and/or turbulence relative to the upper air zone; the treatment system withdrawing air from the lower air zone and supplying purified air to the upper air zone.

In yet another aspect, one embodiment of the invention comprises an operating room air treatment system comprising an upper air zone; a lower air zone comprising air of increased contamination and/or turbulence relative to the upper air zone; and a central operating area; the treatment system withdrawing air from the lower air zone and supplying purified non-turbulent and/or directional air to the upper zone; the purified directional and/or non-turbulent air directed such that it does not enter the central operating area.

In another aspect, one embodiment of the invention comprises an operating room air treatment system comprising a central sterile zone with sterilized surfaces; and a peripheral non-sterile zone comprising non-sterilized surfaces; the treatment system withdrawing air from the non-sterile zone and supplying purified non-turbulent and/or directional air to the non-sterile zone; the purified directional and/or non-turbulent air directed such that it does not enter the sterile zone.

In still another aspect, one embodiment of the invention comprises an operating room air treatment system comprising ceiling-mounted vertical air supply ducts; and lower wall-mounted air return ducts; the treatment system withdrawing air from relative proximity of the return ducts and supplying purified non-turbulent and/or directional air to relative proximity of the supply ducts.

In yet another aspect, one embodiment of the invention comprises an operating room air treatment system comprising an upper area comprising a sterile zone substantially defined as the air volume above sterile horizontal patient drapes; and a lower non-sterile zone substantially defined as the air volume below the drapes; the treatment system withdrawing air from the non-sterile zone and supplying purified non-turbulent and/or directional air to the upper area.

In still another aspect, one embodiment of the invention comprises an operating room air treatment system comprising a central air zone in proximity to a treatment table; and a peripheral zone in proximity to an entry door; the treatment system withdrawing air from the peripheral zone and supplying purified air to the operating room; the purified air being non-turbulent and/or directional and non-crossing of the treatment table; the non-turbulent and/or directional purified air being directionally oblique above the horizontal plane, such that horizontal cross currents are avoided.

In yet another aspect, one embodiment of the invention comprises an operating room air treatment system wherein the operating room comprises a sterile zone with sterilized surfaces; and a non-sterile zone with non-sterilized surfaces; the sterile and non-sterile zones comprising an imaginary border between them; the treatment system withdrawing air from the non-sterile zone and supplying purified non-turbulent and/or directional air to the operating room in a manner that the border between sterile and non-sterile zones is not breached by the purified directional and/or non-turbulent air.

In still another aspect, one embodiment of the invention comprises an operating room air treatment system wherein the operating room comprises a sterile area with sterilized surfaces; and a non-sterile area with non-sterilized surfaces; the treatment system withdrawing air from the non-sterile zone and supplying purified non-turbulent and/or directional air to the operating room in a manner that the purified directional and/or non-turbulent air does not travel from an area of non-sterility to an area of sterility.

In another aspect, one embodiment of the invention comprises an operating room air treatment system wherein the operating room comprises an active surgical procedure in which air contamination due to aerosolized biological substances of patient are released into the room atmosphere; the substances travelling from a high relative air velocity zone to a lower relative velocity zone; the treatment system withdrawing air from the low velocity zone and capturing the substances.

In still another aspect, one embodiment of the invention comprises an operating room air treatment system wherein the operating room comprises relative high air velocity zones; and relative low air velocity zones; the low air velocity and/or velocity zone populated by personnel releasing biological contaminants into the zone; the treatment system withdrawing air from the low air velocity zone and suppling purified non-turbulent and/or directional air to the low air velocity zone.

In yet another aspect, one embodiment of the invention comprises an operating room air treatment system wherein the operating room comprises variable air velocities with a maximum velocity; a minimum velocity; and a mean velocity; the treatment system comprising air flow means to reduce air velocity variation such that the maximum and/or minimum velocity is closer to the mean velocity.

This invention, including all embodiments shown and described herein, could be used alone or together and/or in combination with one or more of the features covered by one or more of the following list of features:

The medical air treatment system wherein the at least one air handler comprises a first air handler for generating the first flow of air and a second air handler for generating the second flow of air, the second air handler having a first air treatment system adapted to receive air from the peripheral zone and decontaminate the air and then exhausting the air back into the peripheral zone such that the air does not flow into the first flow of air and across the table or bed.
  The medical air treatment system wherein the first air handler has a second air treatment system adapted to receive air and deliver the first air flow of air in a substantially decontaminated form substantially vertically to the table or bed.
  The medical air treatment system wherein the first air handler and the second air handlers have different turbulence, velocity or purification characteristics.
  The medical air treatment system wherein the second air handler withdraws air from the peripheral zone, treats the air with the first air treatment system, and then supplies non-turbulent purified air to the peripheral zone.
  The medical air treatment system wherein the first air handler generates a substantially vertical column of air in a central zone that flows towards the patient, and the second air handler generating the second flow of air that is not vertical and generally surrounds the central zone, such that a majority of the second flow of air does not enter the central zone.
  The medical air treatment system wherein the medical air treatment system comprises at least one obstruction for deflecting at least a portion of the first flow of air toward the peripheral zone and generally away from a surgical field having the table or bed and the patient therein.
  The medical air treatment system wherein the medical environment comprises at least one return for returning air from the medical environment to the first air handler and at least one supply for supplying purified non-turbulent and/or directional air to the central zone, the second air handler being adapted to receive air from the peripheral zone or in proximity to the at least one return, treat the received air and return substantially purified and decontaminated air in proximity to the at least one supply.
  The medical air treatment system wherein the peripheral zone defines a substantially non-sterile zone and the central zone defines a substantially sterile zone, the second air handler withdrawing air from the non-sterile zone and treating the air therein and then returning it to the non-sterile zone such that air does not travel the from non-sterile zone to the sterile zone, the sterile zone having the table or bed therein.
  The medical air treatment system wherein the sterile zone is a high velocity zone and the non-sterile zone is a low velocity zone, an airflow rate or velocity in the low velocity zone being lower than an airflow rate or velocity in the high velocity zone, the second air handler withdrawing air from the low air velocity zone, purifying it with the medical air treatment system and supplying purified and non-turbulent and/or directional air to the low air velocity zone.
  The medical air treatment system wherein the operating environment comprises a plurality of airflows having a plurality of velocities comprising at least a maximum velocity, a minimum velocity and a mean velocity, the medical air treatment system having an airflow system or means for controlling air velocity variations such that the maximum velocity and/or minimum velocities are closer to the mean velocity.
  The medical air treatment system wherein the first air treatment system comprises at least one of a biocidal remover, an infrared irradiator, a chemical biocidal remover or a chemical irradiator.
  The operating room air treatment system wherein the second air treatment system comprises a first treatment device for decontaminating an air stream and generating a substantially decontaminated air stream for exhausting into the peripheral zone.
  The operating room air treatment system wherein the first air treatment system comprises a second treatment device for decontaminating an air stream and generating a substantially decontaminated air stream for exhausting into the central zone.
  The operating room air treatment system wherein the second air treatment system is situated in the peripheral zone and receives contaminated air therefrom, the first treatment device treating the air so that the substantially decontaminated air stream may be exhausted into the peripheral zone.
  The operating room air treatment system wherein the first treatment device comprises at least one of a biocidal remover, an infrared irradiator, a chemical biocidal remover or a chemical irradiator.
  The operating room air treatment system wherein the first air treatment system comprises a second treatment device arranged such that its air stream output does not mix in the central zone.
  The operating room air treatment system wherein the first air treatment system comprises a first air handler and the second air treatment system comprises a second air handler, each of the first and second air handlers being configured and arranged such that their respective exhausts do not commingle in the central zone.
  The operating room air treatment system wherein peripheral zone completely surrounds the central zone, the first air treatment system directing a first air flow into the central zone from above the table or bed, the second air treatment system directing a second air flow into the peripheral zone in a manner that it does not cross into the central zone.
  The operating room air treatment system wherein peripheral zone is below the table or bed and the central zone lies above it, the first air treatment system directing a first air flow substantially vertically into the central zone from above the table or bed, the second air treatment system directing a second air flow substantially horizontally under the table or bed and into the peripheral zone in a manner that the second air flow does not cross into the central zone.

The operating room air treatment system wherein the second air treatment system comprises at least one of an adjustable nozzle or duct that is adjustable such that an output of the air flow through the adjustable nozzle or duct may be adjusted so that the output is only directed into the peripheral zone and not the central zone.

The operating room air treatment system where the vertical air flow is created by a first air handler and the horizontal air flow is created by a second air handler, the air handlers having different turbulence, velocity, or purification characteristics.

These and other objects and advantages of the invention will be apparent from the following description, the accompanying drawings and the appended claims.

BRIEF DESCRIPTION OF THE ACCOMPANYING DRAWINGS

DETAILED DESCRIPTION OF THE PREFERRED EMBODIMENTS

Referring now to FIGS. 1-6, a multiple zone air handling system 10 is disclosed. In one embodiment, the multiple zone air handling system 10 is particularly adapted for use in an operating room, patient room or other room 12 where it is desired to provide a multiple zone air handling system 10 that is adapted to control the directional and/or turbulence of air flow and contamination in order to prevent the initiation of undesirable air currents or cross-currents, such as horizontal air currents, which can serve to spread contamination across a surgical field 19 or an operating table 18 in the operating room, patient room or other room 12. The room 12 comprises the operating table 18 where the patient is typically located for surgical procedures. The multiple zone air handling system 10 provides an improved control over direction, pressure, velocity and location of airflows in all the zones of the room 12 in order to eliminate or facilitate reducing patient infection or contamination across the surgical field 19 where a patient (not shown) is located.

Figure 1:
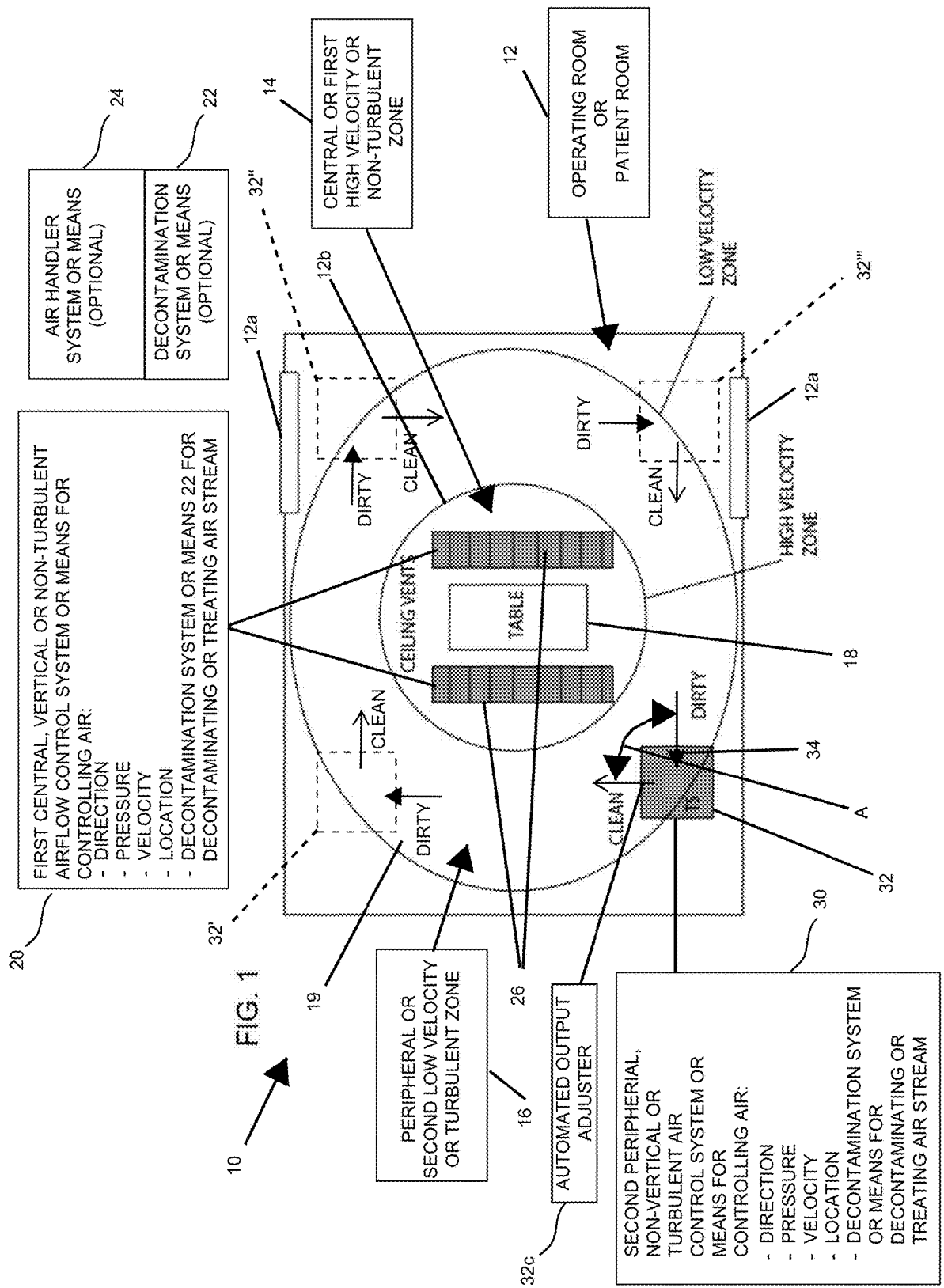
FIG. 1 is a schematic view of an air treatment system in accordance with one embodiment of the invention where air is withdrawn from a low velocity zone in a directional and/or non-turbulent manner so purified air does not enter a high velocity zone.

Referring now to FIG. 1, the room 12 is shown schematically. The room 12 has at least one or more doors 12a for entry and egress into and out of the room 12. It should be appreciated that the room 12 comprises at least one or a plurality of zones. In this regard, note that the room 12 comprises a central or first high velocity or non-turbulent zone 14. It should be understood that in the context of operating room air systems, the non-turbulent air may also tend to be a higher velocity when compared to non-operating room systems.

In FIG. 1, a plan view of the room 12 is shown and the central or first high velocity or non-turbulent zone 14 is generally located in a central or first high velocity or non-turbulent zone 14 of the room 12 where the operating table 18 is located. Surrounding the central or first high velocity or non-turbulent zone 14 is a peripheral or second low velocity or turbulent zone 16 which is separated by an imaginary cylindrical plane 12b. In some embodiments, the peripheral or second low velocity or turbulent zone 16 extends from the floor to the ceiling, and the central or first high velocity or non-turbulent zone 14 extends from the operating table 18 to the ceiling of the room 12. Note that in FIGS. 1-3, the peripheral or second low velocity or turbulent zone 16 is analogous to a donut shape that surrounds the central or first high velocity or non-turbulent zone 14 for ease of illustration and understanding. It should be understood that the central or first high velocity or non-turbulent zone 14 and the peripheral or second low velocity or turbulent zone 16 may be separated differently, as will be illustrated and described later herein relative to FIGS. 4 and 5. This multiple zone air handling system 10 facilitates reducing or eliminating airflow infection by cross-contamination.

In one embodiment, the room 12 comprises a plurality of airflows having a plurality of velocities comprising at least a maximum velocity, a minimum velocity and a mean velocity. The multiple zone air handling system 10 comprises an airflow system or means for controlling air velocity variations such that the maximum velocity and/or minimum velocities are closer to a mean velocity, the maximum velocity being between 1000-3000 CFM and the minimum velocity being less than 500 CFM.

In the past, this donut shape was sometimes referred to as the "dirty donut" because of airborne bacteria that exists in the peripheral or second low velocity or turbulent zone 16. This is where operating room personnel are typically situated. In the past, dirty and contaminated air could pass or cross from the peripheral or second low velocity or turbulent zone 16 to the central or first high velocity or non-turbulent zone 14 and contaminate the central or first high velocity or non-turbulent zone 14, which increases the chances for infection of the patient who is situated on the operating table 18. As is known, operating room airborne bacteria oftentimes derives from operating room personnel located in the peripheral or second low velocity or turbulent zone 16. The peripheral or second low velocity or turbulent zone 16 can be a reservoir for airborne bacteria which can be carried by surface vectors, such as instrumentation, surgical gowns or gloves and the like, to the surgical site where the patient is located.

It should be appreciated that the multiple zone air handling system 10 controls the central or first high velocity or non-turbulent zone 14 and the peripheral or second low velocity or turbulent zone 16 to facilitate reducing cross-contamination of unwanted bacteria and airborne contaminants from the peripheral or second low velocity or turbulent zone 16 into the central or first high velocity or non-turbulent zone 14, thereby reducing or eliminating patient contamination and/or infection.

Figure 2:
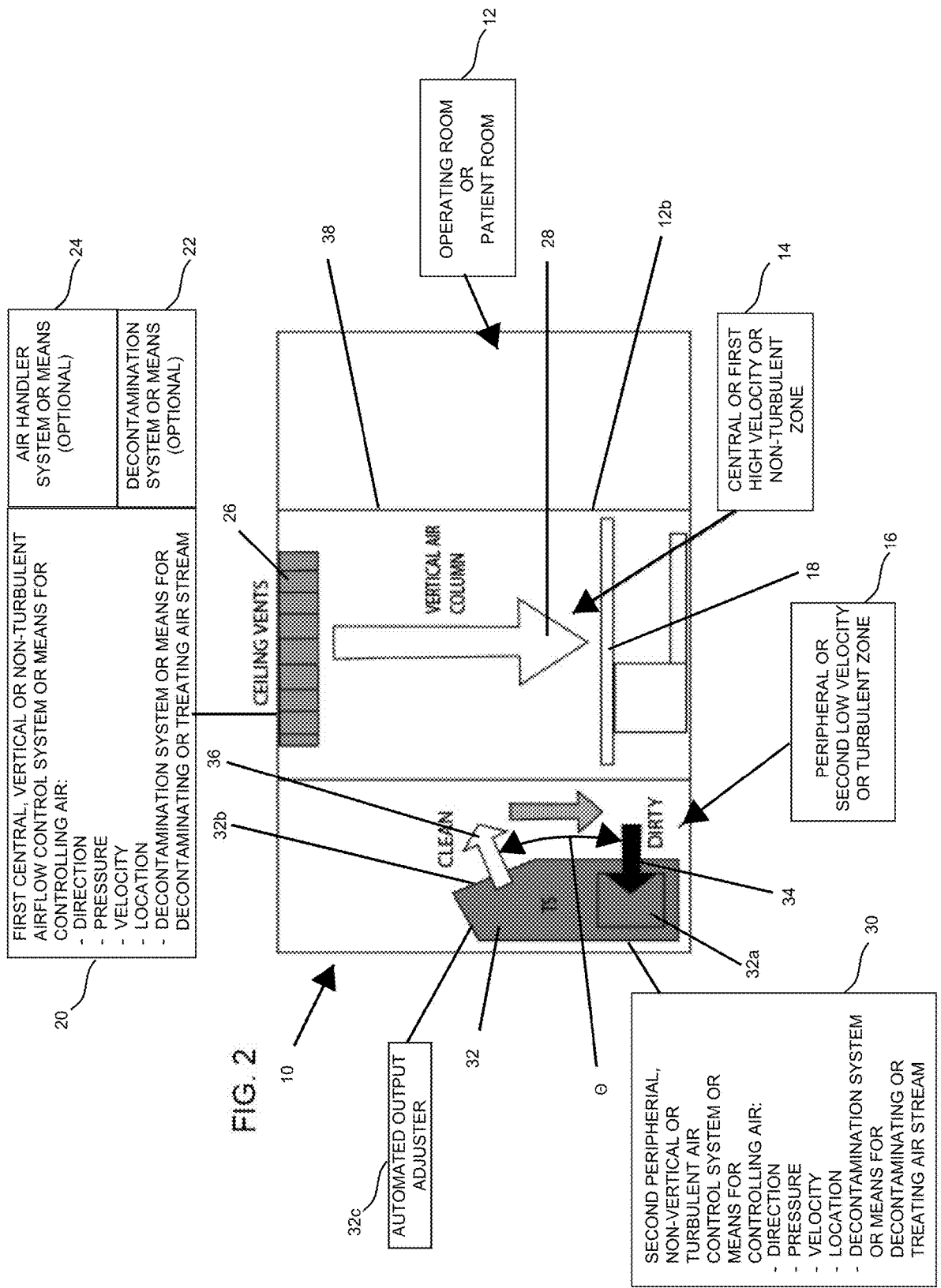
FIG. 2 is an illustration of another embodiment of the air treatment system that withdraws air from a peripheral turbulent zone and supplies non-turbulent purified air to the peripheral turbulent zone.

Referring to FIGS. 1 and 2, notice that the multiple zone air handling system 10 comprises a central, vertical or non-turbulent airflow control system or means 20 for controlling air direction, pressure, velocity, location, decontamination and the like. In one embodiment, the system or means 20 comprises an optional decontamination system or means 22 for decontaminating or treating the air stream from the central, vertical or non-turbulent airflow control system or means 20. In the illustration being described, the decontamination system or means 22 is adapted for decontaminating and treating the air stream from an air handler 24 (FIG. 1) that is either resident in the room 12 or remote therefrom. The air handler 24 generates an airstream that passes through the at least one or a plurality of ceiling vents 26 in the illustration being described.

As best illustrated in FIG. 2, notice that the central, vertical or non-turbulent airflow control system or means 20 and air handler 24 generate a central, vertical and/or non-turbulent air column 28 that, in the illustration being described, has been decontaminated and passes vertically (as viewed in FIG. 2) downward from, for example, one or more wall or ceiling vents 26 toward the patient (not shown) who is situated on the operating table 18.

Substantially simultaneously, the multiple zone air handling system 10 also comprises a second peripheral, non-vertical or turbulent air control system or means 30 for controlling air that controls direction, pressure, velocity, location and also comprises a decontamination system or means for decontaminating or treating the air stream. In this embodiment, the second peripheral, non-vertical or turbulent air control system or means 30 comprises the air handler and decontamination system 32 as shown in FIG. 1. The air handler and decontamination system 32 comprises a bottom inlet 32a (FIG. 2). As best illustrated in FIG. 2, the bottom inlet 32a receives dirty air 34 from the peripheral or second low velocity or turbulent zone 16 and then processes, decontaminates and treats the air and then exhausts it through an outlet or exhaust 32b into the peripheral or second low velocity or turbulent zone 16. In the illustration being described, the air handler and decontamination system 32 could be the ILLUVIA® decontamination air handler product available from Aerobiotix, Inc. of Miamisburg, Ohio. In the illustration being described, one suitable air handler and decontamination system 32 may include the system, apparatus or features of the air handler and irradiation devices shown in U.S. Pat. Nos. 9,433,693; 9,457,119; 9,764,054; 10,039,854; 10,532,122 and 10,549,007; as well as U.S. Patent Publication Nos. 2018/0133084; 2018/0133355; 2018/0264391; 2019/0099050 and 2020/0047094, all of which are assigned to the same assignee as the present application and are incorporated herein by reference and made a part hereof.

It should also be appreciated that one or more of the air handlers 32 have a system or means for directing the airflow in a desired direction. For example, it is contemplated that an air handler and decontamination system 32 may have an exhaust 32b (FIG. 2) which may also comprise features of U.S. Publication No. 2018/0133084, which is assigned to the Assignee of the present application and which is incorporated herein by reference and made a part hereof. Thus, it is contemplated that the exhaust 32b may have an adjustable exhaust, air hose or duct that can be positioned such that the output from the second air handler 32 flows into the peripheral or second low velocity or turbulent zone 16 as previously explained. Alternatively, the multiple zone air handling system 10 may incorporate an automated output adjuster 32c for automatically adjusting the directional output of the air as it flows out of the air handler and decontamination system 32. Thus, it should be understood that the multiple zone air handling system 10 may comprise the second air handler 32 that may comprise at least one of an adjustable nozzle or duct (not shown) that is adjustable such that an output of the airflow through the adjustable nozzle or duct may be adjusted so that the exhaust 32b is only directed into the peripheral or second low velocity or turbulent zone 16 and not the first high velocity or non-turbulent zone.

Note from the FIGS. 1 and 2 that in this illustration, the air handler and decontamination system 32 is particularly adapted to treat and control the airflow in the peripheral or second low velocity or turbulent zone 16 because, as illustrated by the double arrow A in FIG. 1, the air handler and decontamination system 32 takes in dirty air 34, processes and decontaminates the dirty air 34 and exhausts clean, decontaminated air.

It is important to note the angular relationship of the dirty air 34 and the clean air 36 illustrated in FIG. 1. Note that in this illustration, they are generally offset by approximately ninety (90) degrees, as indicated by the double arrow A in FIG. 1. Advantageously, the second peripheral, non-vertical or turbulent air control system or means 30 decontaminates and cleans the air in the peripheral or second low velocity or turbulent zone 16 and delivers or returns the cleaned air back to the peripheral or second low velocity or turbulent zone 16. It is extremely important to note that the second peripheral, non-vertical or turbulent air control system or means 30 and the air handler and decontamination system 32 is oriented to deliver the cleaned air at a desired velocity to the peripheral or second low velocity or turbulent zone 16 and at least a majority of the delivered decontaminated or clean air does not breach the imaginary cylindrical plane 12b and enter into the area between the central or first high velocity or non-turbulent zone 14. In one embodiment, the decontaminated air also does not traverse the peripheral or second low velocity or turbulent zone 16 and the imaginary cylindrical plane 12b (FIG. 1).

Referring back to FIG. 2, notice that a second angle of delivery of the cleaned and processed air is illustrated by the angle Θ. The decontaminated air stream may be directed in an oblique vector from 1 to 89 degrees upward from horizontal. A second air treatment system may be situated in the peripheral zone and receive contaminated air flow therefrom which comprises an inflow vector originating at a point beneath the table 18.

In the illustration being described, note that the air handler and decontamination system 32 angles the clean air 36 upwards as illustrated, but it should be understood that the air handler and decontamination system 32 could deliver the air downwards, horizontally or directly vertically into the peripheral or second low velocity or turbulent zone 16. Preferably, the clean air 36 in the embodiment shown in FIG. 2 moves obliquely from the air handler and decontamination system 32 and does not move horizontally (as viewed in FIG. 2) into the central or first high velocity or non-turbulent zone 14 or across the operating table 18 and the patient so as to minimize the possibility of moving or transferring contaminated or dirty air 34 from the peripheral or second low velocity or turbulent zone 16 across the surgical field 19. This substantially minimizes or reduces the chance for unwanted bacteria and contaminants to reach the surgical field 19 and the patient who is on the operating table 18 during a surgical procedure.

It should be appreciated that the outflow of the central, vertical or non-turbulent airflow control system or means 20 and the second peripheral, non-vertical or turbulent air control system or means 30 is also directional. The outflow of the central, vertical or non-turbulent airflow control system or means 20 is directional and/or non-turbulent in nature in order to prevent the initiation of undesired horizontal air currents from the peripheral or second low velocity or turbulent zone 16, which can serve to spread contamination across the surgical field 19. Notice also that the outflow of the second peripheral, non-vertical or turbulent air control system or means 30 is into the peripheral or turbulent zone and away from the central or first high velocity or non-turbulent zone 14 in order to prevent or facilitate preventing the initiation of undesirable horizontal (as viewed in FIG. 2) air current into the central or first high velocity or non-turbulent zone 14.

It should be understood that each of the central, vertical or non-turbulent airflow control system or means 20 and the second peripheral, non-vertical or turbulent air control system or means 30 may comprise at least one or a plurality of the air handlers and/or decontamination systems 32. For example, the air handler and decontamination systems 24 and 32 could be the decontaminating air handling system available from Aerobiotix, Inc. of Miamisburg, Ohio, under the trademark ILLUVIA®. More than one of these air handler and decontamination systems 32 may be situated in the peripheral or second low velocity or turbulent zone 16. For example, a second 32', third 32" and/or fourth 32''' device may be situated or operatively associated with each corner of the room 12, as indicated in phantom in FIG. 1. Alternatively, two, three or more air handler and decontamination systems 32 could be situated across or cattycorner from each other. FIG. 1 illustrates in phantom one or more additional air handler and decontamination systems 32', 32" and 32''' and these are labeled with the same part number except that one or more prime marks have been added to the part number as shown. In other words, the multiple zone air handling system 10 may comprise a plurality of second peripheral, non-vertical or turbulent air control system or means 30 which facilitate decontaminating and cleaning the air in the peripheral or second low velocity or turbulent zone 16 and returning it to that zone in a manner such that it does not cross the surgical field 19 as mentioned earlier herein. As with the air handler and decontamination system 32, all air handler and decontamination systems 32, 32', 32" and 32''' withdraw air from the peripheral or second low velocity or turbulent zone 16 and supply non-turbulent purified air to the peripheral or second low velocity or turbulent zone 16 as shown. Each air handler and decontamination systems 32, 32', 32" and 32''' may have the features mentioned earlier, such as a directional nozzle and the like.

Figure 3:
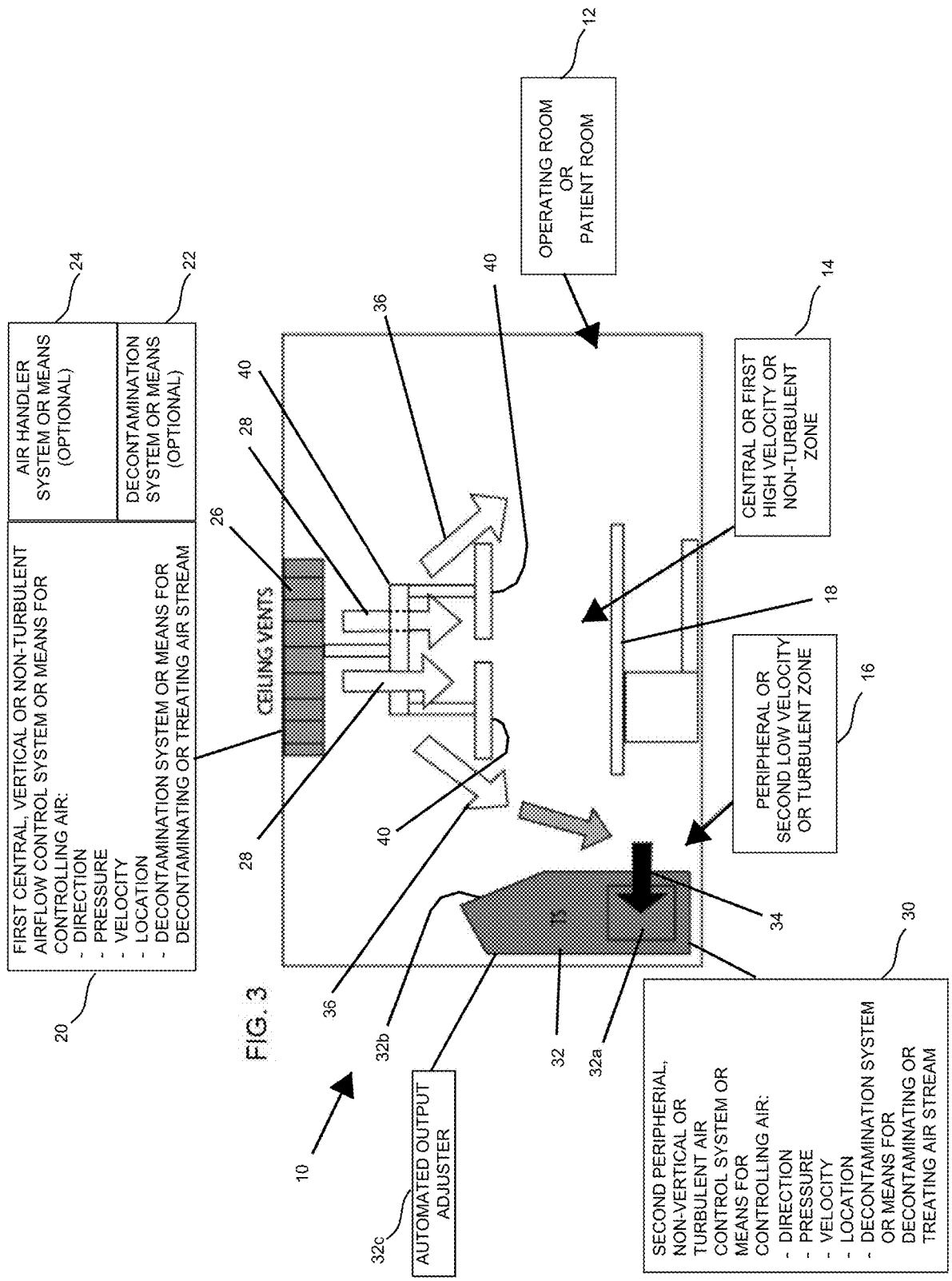
FIG. 3 is another embodiment of the air treatment system utilizing deflectors to withdraw deflected air and supply the purified, non-turbulent air to the operating room.

Referring now to FIG. 3, another illustrative embodiment is shown. In this embodiment, the multiple zone air handling system 10 deflects or diverts air emanating or being exhausted from the at least one or plurality of ceiling vents 26 away from the operating table 18 and patient. Notice in FIG. 3 that as the clean air 36 is exhausted from the at least one or a plurality of ceiling vents 26 the air is deflected by at least one or a plurality of obstructions or deflectors 40, which in the illustration being described are generally planar surfaces that the clean air 36 emanating from the at least one or a plurality of ceiling vents 26 engage. This, in turn, causes the air to be deflected toward the peripheral or second low velocity or turbulent zone 16 as shown. The air of the air handler and decontamination system 32 ultimately is received in the peripheral or second low velocity or turbulent zone 16 and captured by the air handler and decontamination system 32 as shown. Note that as the air gradually passes into the peripheral or second low velocity or turbulent zone 16 that it becomes "dirtier" and more contaminated until ultimately it reaches the air handler and decontamination system 32 where it is received, decontaminated and treated and then ultimately returned to the peripheral or second low velocity or turbulent zone 16 as described earlier herein.

It should be understood that the central, vertical or non-turbulent airflow control system or means 20 and the second peripheral, non-vertical or turbulent air control system or means 30 and their respective air handlers 24 and 32 and the like may have different turbulence, velocity, direction, pressure, location and decontamination or purification characteristics. In other words, they do not have to be identical systems and in a preferred embodiment the systems are not identical. It should be noted that in the case of two systems 20 or 30, the first system 20 would be typically mounted and would draw air from a central system that is located in the ceiling and supplies air in a vertical, down-going fashion. The second system 30 or plurality of systems are typically mobile and draw air from inside the room, sets upon the floor and supplies air in multiple potential directions.

Notice in FIG. 3 that the deflectors 40 are generally substantially orthogonal with respect to a main axis of the airflow from the at least one or plurality of ceiling vents 26 such that the deflectors 40 deflect the non-turbulent air column 28 to the peripheral or second low velocity or turbulent zone 16 so that the central, vertical or non-turbulent airflow control system or means 20 can withdraw air from the deflected air and supply purified, non-turbulent and clean air 36 to the room 12. Although not shown, the deflectors 40 may be ceiling lights, baffles, deflective shields or planar members or other type of deflectors or baffling systems adapted to direct the airflow away from the operating table 18 and patient and to the peripheral or second low velocity or turbulent zone 16 where the airflow can be treated by the air handler and decontamination system 32. They could also be arranged obliquely or angled relative to the airflow path to further facilitate the air passing into the central or first high velocity or non-turbulent zone 14. Thus, in the illustration being described, the deflectors 40 could direct the clean air 36 to a predetermined location, preferably in the peripheral or second low velocity or turbulent zone 16. While the predetermined location in the preferred embodiment is the peripheral or second low velocity or turbulent zone 16, in one illustrative embodiment, the air from the air handler and decontamination system 32 is directed generally toward the at least one or plurality of ceiling vents 26 where it becomes co-mingled with the clean air 36 being delivered or exhausted into the room 12 through the at least one or plurality of ceiling vents 26, as generally illustrated in FIG. 4, which will now be described.

Figure 4:
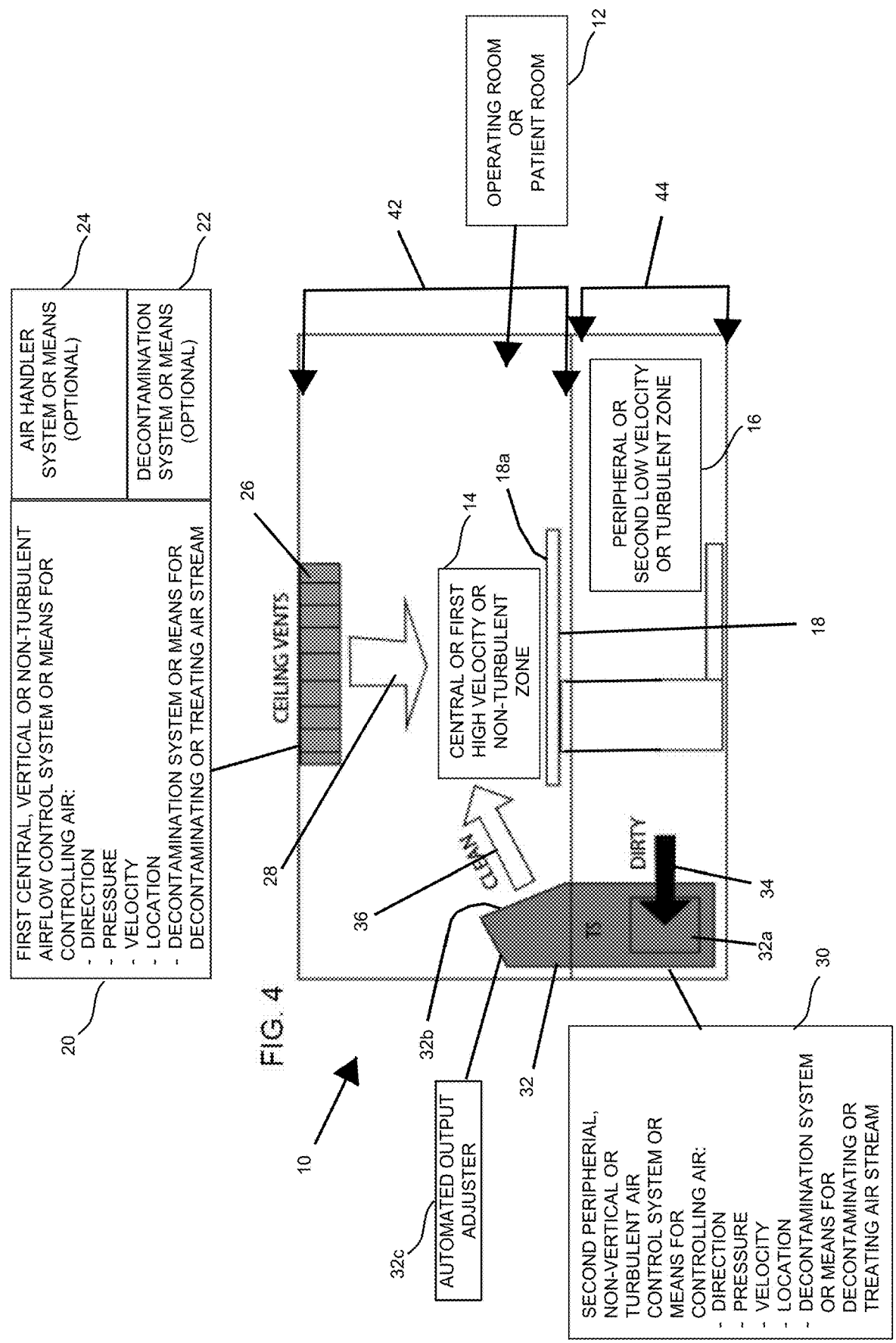
FIG. 4 illustrates a lower air zone that comprises air of increased contamination and/or turbulence relative to an upper air zone and wherein the treatment system withdraws air from the lower air zone and supplies purified air to the upper air zone.

FIG. 4 shows another illustrative embodiment wherein the multiple zone air handling system 10 segments the room 12 into a plurality of zones as with the other embodiments described herein. In this embodiment, the multiple zone air handling system 10 segments the room 12 into an upper zone 42 and a lower zone 44. In the illustration being described, the upper zone 42 is the non-turbulent, high velocity clean zone and the lower zone 44 is the turbulent, low velocity zone. Notice that the top surface 18a of the operating table 18 is situated in the upper zone 42 as shown. During operation, the central, vertical or non-turbulent airflow control system or means 20 and air handler 24 generate the high velocity and clean airflow into the upper zone 42 and direct it generally vertically (as viewed in FIG. 4) downwards toward the patient as illustrated. The dirty zone is situated in the lower zone 44 which the second peripheral, non-vertical or turbulent air control system or means 30 and air handler and decontamination system 32 treat by receiving the dirty air 34 in a bottom inlet 32*a* of the air handler and decontamination system 32. As with the embodiment described earlier in FIG. 2, the air handler and decontamination system 32 receives dirty air 34 that is generally flowing horizontally below the top surface 18*a* of the operating table 18 and in the bottom inlet 32*a* and processes, decontaminates and/or treats the air and returns it through the outlet or exhaust 32*b* and into the central or first high velocity or non-turbulent zone 14 and the upper zone 42. In this embodiment, note that the air does not enter the central or first high velocity or non-turbulent zone 14 and remains peripheral. In the embodiment of FIG. 4, the air from the air handler 24 does not mix with the clean air from the ceiling vents. The emanating air runs parallel to the ceiling vents and is not perpendicular and does not cross the air streams.

Advantageously, the embodiment of FIG. 4 provides a lower air zone 44 that comprises increased contamination and/or turbulence relative to the upper zone 42, and the air handler and decontamination system 32 withdraws the dirty air 34 from the lower zone 44 and supplies purified air to the upper zone 42 as shown.

Figure 5:
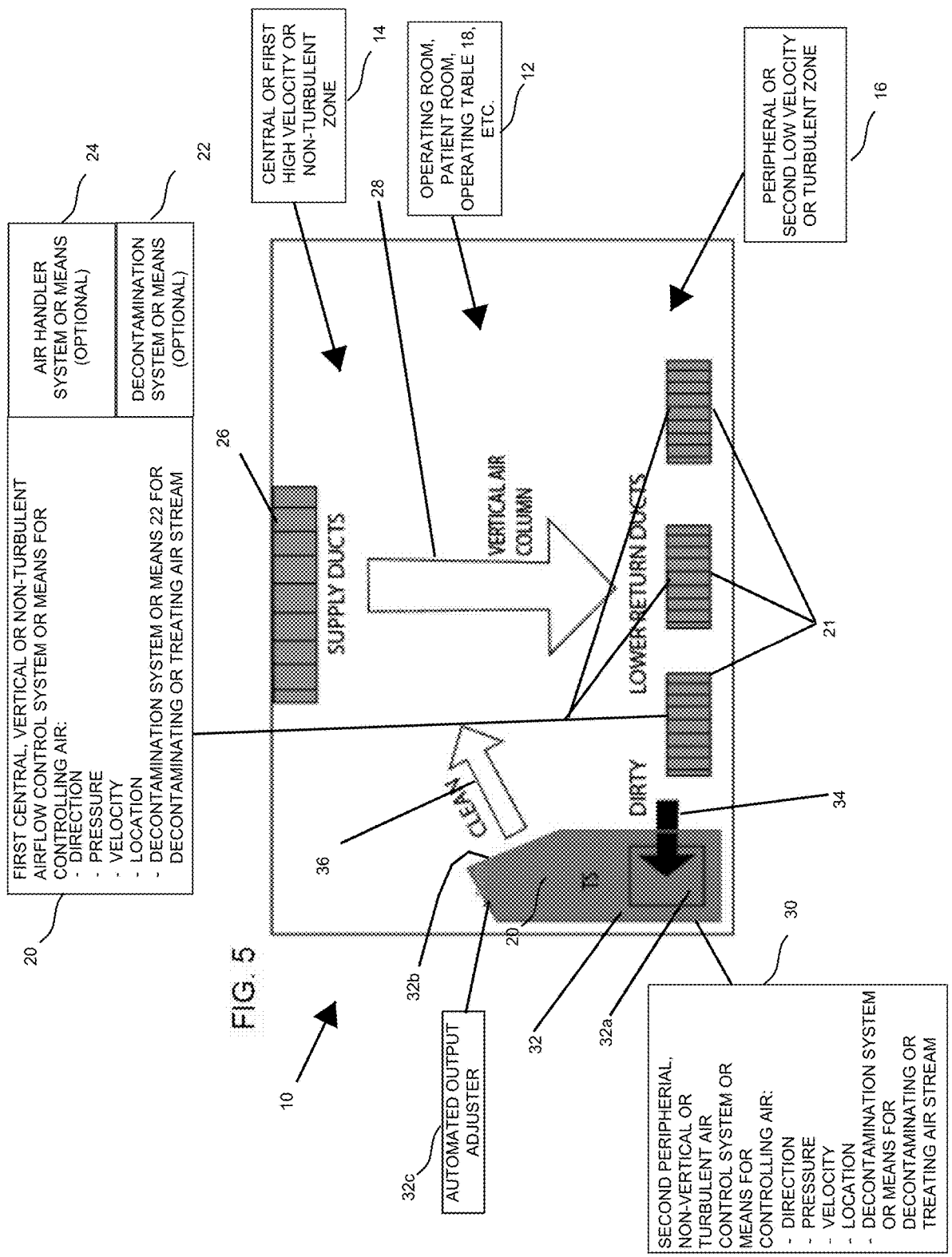
FIG. 5 is another embodiment of the air treatment system that withdraws air from relative proximity of return ducts and supplies purified non-turbulent and/or directional air to a relative proximity of supply ducts.

FIG. 5 illustrates another embodiment wherein the lower return ducts 21 capture air and return it to the air handler 24 of the central, vertical or non-turbulent airflow control system or means 20. Note that the lower return ducts 21 traditionally capture air from the room 12, including air that has been exhausted from the air handler 24. In this embodiment, the second peripheral, non-vertical or turbulent air control system or means 30 and air handler and decontamination system 32 supply purified, non-turbulent and/or directional air to the proximity of the at least one or plurality of ceiling vents 26 as illustrated so that air descending from the at least one or plurality of ceiling vents 26 is in a generally vertical air column 28 as illustrated in FIG. 5. It is important to note that in this and the other embodiments, the air is not permitted to pass horizontally across the operating table 18 for the reasons mentioned earlier namely because such flow would likely force or draw unwanted contaminants into and/or across the surgical field 19 and the operating table 18. The system 30 draws air from the dirty portion of the room, which is below the surface of the operating table 18. It creates an oblique rather than a horizontal air flow. This prevents blowing contaminated air on a person adjacent to the system 30 and spreading contamination to the operating table 18.

Figure 6:
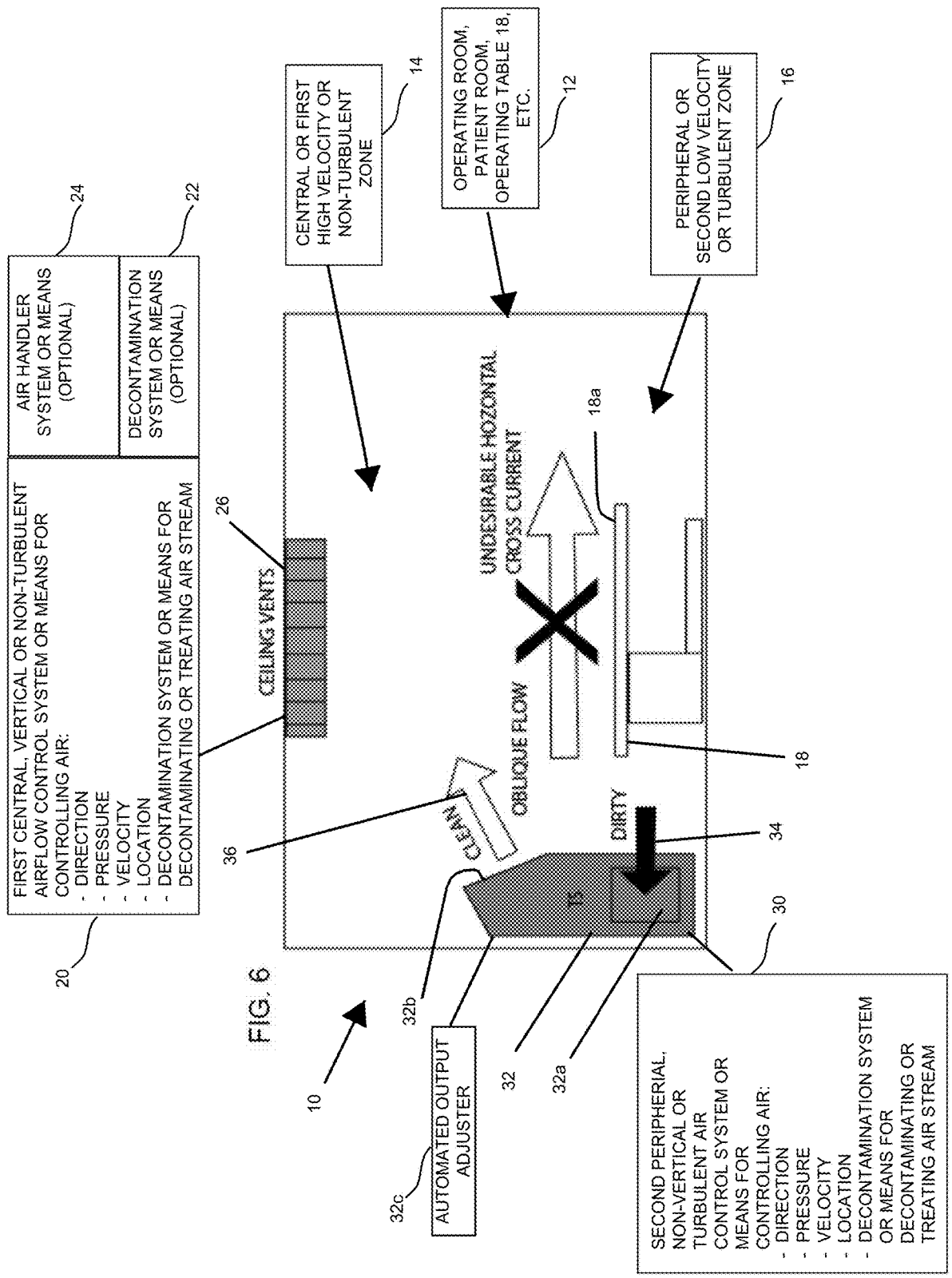
FIG. 6 is another embodiment of the air treatment system where non-turbulent and/or directional purified air is directionally oblique above a horizontal plane in order to avoid horizontal cross-currents.

FIG. 6 illustrates one of the goals of the embodiments described herein in that the non-turbulent and/or directional purified air is directed directionally obliquely above the horizontal plane such that the horizontal cross-currents are avoided. Accordingly, one feature of the embodiment being described is that the air handler and decontamination system 32 directs processed and decontaminated air generally obliquely so that the unwanted horizontal cross-currents are avoided.

Figure 7:
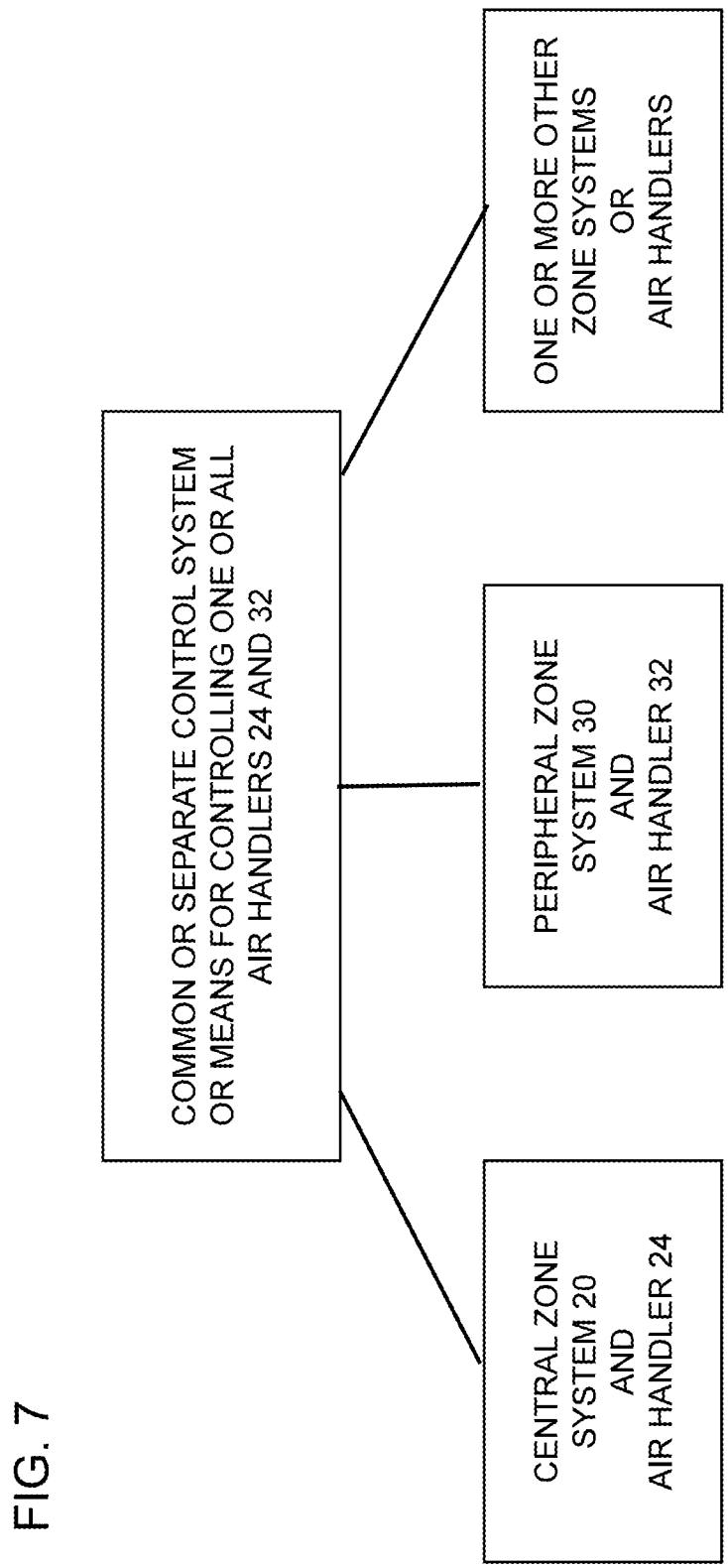
FIG. 7 is a schematic view illustrating an optional common control for controlling all decontaminating system and/or air handlers.

FIG. 7 illustrates a schematic diagram illustrating an optional common control for controlling all decontaminating system and/or air handlers.

ADDITIONAL CONSIDERATIONS

1. It should be understood that the central, vertical or non-turbulent airflow control system or means 20 and the second peripheral, non-vertical or turbulent air control system or the second peripheral, non-vertical or turbulent air control system or means 30 each incorporate the decontamination system, such as the ILLUVIA® system, available from Aerobiotix, Inc. located in Miamisburg, Ohio. For example, the decontamination systems or means may comprise ultraviolet radiation (such as one or more ultra-violet lamps), infrared radiation, filtration, such as by use of HEPA filters, chemical or germicidal treatment system or other means adapted to treat the airflow as it passes through the central, vertical or non-turbulent airflow control system or means 20 and the second peripheral, non-vertical or turbulent air control system or the second peripheral, non-vertical or turbulent air control system or means 30. In the illustration being described, the air handler 24 and the air handler and decontamination system 32 each comprise both filtration and UV radiation which filter and process or treat the air stream flowing through the air handlers 24 and air handler and decontamination system 32 in a manner conventionally known. It should be appreciated that other treatment systems like mechanical, radiation chemical or electrical decontamination can be utilized.

Thus, it should be understood that the means for treating the airflow in the central, vertical or non-turbulent airflow control system or means 20 and the second peripheral, non-vertical or turbulent air control system or the second peripheral, non-vertical or turbulent air control system or means 30 could comprise the ILLUVIA® air handler system and technology available from Aerobiotix, Inc., but it could also comprise other means for filtering, treating and disinfecting or decontaminating the air stream.

2. Advantageously, the system and means described herein is particularly adapted to control airflow in the surgical field 19 and in the central or first high velocity or non-turbulent zone 14. By controlling the airflow, direction, pressure, velocity and location of the air stream as it flows in the central or first high velocity or non-turbulent zone 14 and the peripheral or second low velocity or turbulent zone 16, the purity of the air in the central or first high velocity or non-turbulent zone 14 is improved and the actual and potential cross-contamination from the peripheral or second low velocity or turbulent zone 16 into the central or first high velocity or non-turbulent zone 14 is reduced or eliminated altogether. In contrast, in the prior art, the flow tended to be generally horizontal and oftentimes caused dirty air adjacent to the central or first high velocity or non-turbulent zone 14 or in the peripheral or second low velocity or turbulent zone 16 to cross or pass into the central or first high velocity or non-turbulent zone 14 where the patient is located which substantially increases the probability of adverse effects, such as patient infection from contamination received from the peripheral or second low velocity or turbulent zone 16.

3. In the illustration being described, the air handler and decontamination system 32 is mobile and transportable and thus can be situated, arranged or adjusted such that its bottom inlet 32*a* is operatively positioned in the peripheral or second low velocity or turbulent zone 16 while its outlet or exhaust 32*b* is also positioned such that the direction of the clean air 36 from the exhaust 32*b* is also directed to flow into the peripheral or second low velocity or turbulent zone 16 such that the output does not cross-feed horizontally (as viewed in FIG. 2, for example) into the central or first high velocity or non-turbulent zone 14 where the surgical field 19 is located. The features of U.S. Publication No. 2018/0133084 may be used to assist with directing the airflow and/or the directional control may be automated.

4. Alternatively, the decontamination system or means and air handlers 24 and air handler and decontamination system 32 may be non-mobile, as with the system 24. They may also be portable or mobile as described. Alternatively, the air handler and decontamination system 32 could also be a permanent fixture or part of the infrastructure or building in which the room 12 is located.

5. Advantageously, the multiple zone air handling system 10 and methods described herein provide non-turbulent airflow in the surgical field 19 and improve or increase the probability of the surgical field 19 being, remaining or becoming sterile and non-contaminated. The system and means also facilitates ensuring that contaminated air from the peripheral or second low velocity or turbulent zone 16 is not directed to or around a patient situated on the operating table 18. As mentioned earlier herein relative to the embodiment of FIG. 5, the multiple zone air handling system 10 may comprise the ceiling-mounted vertical air supply ducts 26 and lower wall mounted air return ducts 21. Applicant has found that the air handler and decontamination system 32 withdraws air from relative proximity of the return ducts 21 and supplies purified, non-turbulent and/or directional air to relative proximity of the supply ducts 26. In the embodiment of FIG. 4, the upper area 42 comprises the sterile zone substantially defined as the air volume above the sterile horizontal patient drapes, and a lower non-sterile zone 44, which is preferably below the top surface 18a of the table 18, that defines the air volume below the drapes, with that air volume being more contaminated with unwanted airborne bacteria and the like than what is present in the upper area 42. Again, advantageously the system withdraws air from the non-sterile lower zone and returns purified air to the upper zone.

6. As mentioned earlier, the central or first high velocity or non-turbulent zone 14 is in proximity to the table 18 and the peripheral or second low velocity or turbulent zone 16 is in proximity to the doors 12a where people enter the room 12. Advantageously, the multiple zone air handling system 10 withdraws air from the peripheral or second low velocity or turbulent zone 16 and supplies purified air the room 12 and the surgical field 19 such that the purified air is non-turbulent and/or directional and non-crossing of the table 18.

7. As also mentioned earlier, it may be advantageous to disrupt the airflow in the central or first high velocity or non-turbulent zone 14 with deflectors 40 or obstructing features, such as lights, equipment booms, personnel, baffles or other airflow interrupters or deflectors as mentioned earlier. In general, these obstructions are substantially orthogonal and deflect the air column to the peripheral or second low velocity or turbulent zone 16 where the multiple zone air handling system 10 withdraws the deflected air and supplies purified, non-turbulent air to the room 12 and the surgical field 19.

8. Note that it is not uncommon that in both the central or first high velocity or non-turbulent zone 14 and the peripheral or second low velocity or turbulent zone 16, non-sterilized surfaces may be present, particularly in the peripheral or second low velocity or turbulent zone 16. Again, the multiple zone air handling system 10 withdraws air from the peripheral or second low velocity or turbulent zone 16 and supplies purified, non-turbulent and/or directional air to the central or first high velocity or non-turbulent zone 14. The purified directional and/or non-turbulent air may be directed in the peripheral or second low velocity or turbulent zone 16 such that it does not enter the central or first high velocity or non-turbulent zone 14. Note that the central or first high velocity or non-turbulent zone 14 is in proximity and associated with the operating table 18 while the peripheral or second low velocity or turbulent zone 16 is in proximity to the entry door or doors 12a. The multiple zone air handling system 10 withdraws air from the peripheral or second low velocity or turbulent zone 16 and supplies purified air to the peripheral or second low velocity or turbulent zone 16 which is in proximity to one or more entry doors 12a into the room 12. Again, the multiple zone air handling system 10 withdraws air from the peripheral or second low velocity or turbulent zone 16 and supplies purified air to the room 12, with the purified air being non-turbulent and/or directional and non-crossing of the treatment table 18. The non-turbulent and/or directional purified air is both directionally oblique above the horizontal plane such that horizontal cross-currents across the table 18 are avoided.

9. As mentioned previously, the central or first high velocity or non-turbulent zone 14 may be considered a sterile zone with sterilized surfaces while the peripheral or second low velocity or turbulent zone 16 may be considered a non-sterile zone with non-sterilized surfaces such as equipment surfaces, lighting surfaces, floors, walls, ceilings and the like. The sterile and non-sterile zones have an imaginary border between identified as part 38 in FIG. 1, and the multiple zone air handling system 10 withdraws air from the non-sterile zone and supplies purified non-turbulent and/or directional air to the room 12 in a manner that the border between the sterile zone and the non-sterile zone is not breeched by the purified directional and/or turbulent air.

10. Stated another way, the multiple zone air handling system 10 withdraws air from the non-sterile zone and supplies purified, non-turbulent and/or directional air to the room 12 in a manner that the purified non-turbulent and/or directional air does not travel from the non-sterile zone to an area of sterility.

11. The room 12 comprises an active surgical procedure in which air contamination due to aerosolized biological substances of the patient are released into the room atmosphere and the substances travel from a high relative air velocity zone to a lower relative velocity zone and the multiple zone air handling system 10 withdraws air from said low velocity zone and captures the substances.

12. As mentioned earlier in one embodiment, the multiple zone air handling system 10 is particularly adapted for use with the room 12 that has at least one relatively high air velocity zone and at least one relatively low air velocity zone. The low air velocity zone is typically populated by personnel who release biological contaminants into the low air velocity zone. Advantageously, the multiple zone air handling system 10 withdraws air from the low air velocity zone and supplies purified non-turbulent and/or directional air to the low air velocity zone in a manner that preferably does not breach the central or first high velocity or non-turbulent zone 14.

13. In still another embodiment, the multiple zone air handling system 10 is also adapted for use in the room 12 that comprises variable air velocities with a maximum velocity, a minimum velocity and a mean velocity. The multiple zone air handling system 10 may also comprise air flow means to reduce air velocity variation such that the maximum and/or minimum velocity is closer to the mean velocity. The multiple zone air handling system 10 comprises the air handler and decontamination system 32 and air handler 24 that reduce air velocity variation such that the maximum and/or minimum velocity is closer to the mean velocity.

14. Another embodiment illustrates the multiple zone air handling system 10 comprising a substantially vertical airflow zone and a substantially horizontal airflow zone. The multiple zone air handling system 10 controls the airflow from the air handlers 24 and air handler and decontamination system 32 such that the substantially vertical airflow zone is located centrally in the room 12 and the substantially horizontal airflow zone is located peripherally in the room 12. In other words, the central or first high velocity or non-turbulent zone 14 has a vertical air column as viewed in FIG. 2 and the peripheral or second low velocity or turbulent zone 16 generally causes airflow to be substantially horizontal and generated in a manner that it does not mix the dirty air from the peripheral or horizontal zone with the clean central air in the central or first high velocity or non-turbulent zone 14.

15. It should be noted that special directional attachments can be provided in order to create a desired or predetermined laminar or non-turbulent airflow.

16. Multiple peripheral systems can be provided in large rooms in order to ensure that the airflows do not cross, the output of the peripheral system should be kept as a non-crossing vector, for example, the central system 20.

17. It should be noted that one advantageous advantage of this system and method is that the output may be pointed parallel to the table, whereas some systems in the past have been placed pointed away from the table.

18. It should be appreciated that the one or more treatment devices may also comprise at least one of a mechanical filter, biocidal device or an ultraviolet irradiator.

19. As illustrated in FIG. 7, the multiple zone air handling system 10 can house multiple zones, multiple system 20 and 30, each of which may be separately controlled or under the common control of a control system having a microphone and control adapted to control these devices. Such a control is available from Aerobiotix, Inc. located in Miamisburg, Ohio.

Advantageously, the embodiments shown and described herein could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. An operating room air treatment system comprising:
a vertical air flow zone; and
a non-vertical air flow zone;
wherein said vertical air flow zone is located centrally in the room and said non-vertical air flow zone is located peripherally in said room;
wherein said vertical air flow zone is created by a first air handler and said non-vertical air flow zone is created by a second air handler;
said second air handler is spaced apart from said first air handler and said vertical air flow zone and comprises a decontamination system that decontaminates and cleans the air in said non-vertical air flow zone and delivers or returns the cleaned air back to said non-vertical air flow zone so that at least a majority of the delivered decontaminated or clean air does not breach the vertical air flow zone, each of said first and second air handlers having a blower;
wherein said decontamination system comprises both filtration and ultraviolet (UV) radiation which filters or processes the air flowing through said second air handler; and
wherein 100 percent of the decontaminated and cleaned air from said second air handler is returned to the non-vertical air flow zone.

2. The operating room air treatment system of claim 1 where said vertical air flow zone is created by said first air handler and said non-vertical air flow zone is created by said second air handler, said air handlers having different turbulence, velocity, or purification characteristics.

3. The operating room air treatment system as recited in claim 1 wherein said second air handler comprises a first treatment device for decontaminating an air stream and generating a substantially decontaminated air stream for exhausting into said non-vertical air flow zone.

4. The operating room air treatment system as recited in claim 1 wherein said decontaminated air stream is directed in an oblique vector from 1 to 89 degrees upward from horizontal.

5. The operating room air treatment system as recited in claim 1 wherein said second air handler receives contaminated air flow therefrom, said contaminated air flow comprising an inflow vector originating at a point beneath a table or bed.

6. The operating room air treatment system as recited in claim 5 wherein said inflow vector and said decontaminated air stream are orthogonal to each other in a horizontal plane.

7. The operating room air treatment system as recited in claim 1 wherein said first air handler comprises at least one of a mechanical filter, biocidal device or an ultraviolet irradiator.

8. The operating room air treatment system as recited in claim 1 wherein said first air handler comprises a second treatment device arranged such that its air stream output does not mix in said vertical air flow zone.

9. The operating room air treatment system as recited in claim 1 wherein each of said first and second air handlers being configured and arranged such that their respective exhausts do not commingle in said vertical air flow zone.

10. The operating room air treatment system as recited in claim 1 wherein said non-vertical air flow zone completely surrounds said vertical air flow zone, said first air handler directing a first air flow into said vertical air flow zone from above a table or bed, said second air handler directing a second air flow into said non-vertical air flow zone in a manner that it does not cross into said vertical air flow zone.

11. The operating room air treatment system as recited in claim 1 wherein said non-vertical air flow zone is below a table or bed and said vertical air flow zone lies above it, said first air handler directing a first air flow substantially vertically into said vertical air flow zone from above a table or bed, said second air handler directing a second air flow substantially horizontally above said a or bed and into said non-vertical air flow zone in a manner that said second air flow does not cross into said vertical air flow zone.

12. The operating room air treatment system as recited in claim 1 wherein said second air handler comprises at least one of an adjustable nozzle or duct that is adjustable such that an output of the air flow through said adjustable nozzle or duct may be adjusted so that said output is only directed into said non-vertical air flow zone and not said vertical air flow zone.

13. The operating room air treatment system as recited in claim 1 wherein the second air handler is mobile.

* * * * *